(12) United States Patent
Vorm et al.

(10) Patent No.: US 8,074,494 B2
(45) Date of Patent: Dec. 13, 2011

(54) PLUGGED FLOW 2D CHROMATOGRAPHY

(75) Inventors: Ole Vorm, Odense M (DK); Michael Barrett Andersen, Vejle (DK); Ole Tang Sørensen, Odense SØ (DK); Søren Theodorsen, Odense C (DK)

(73) Assignee: Proxeon Biosystems A/S, Odense M (DK)

( * ) Notice: Subject to any disclaimer, the term of this patent is extended or adjusted under 35 U.S.C. 154(b) by 513 days.

(21) Appl. No.: 12/270,107

(22) Filed: Nov. 13, 2008

(65) Prior Publication Data

US 2009/0145203 A1  Jun. 11, 2009

Related U.S. Application Data

(60) Provisional application No. 61/012,547, filed on Dec. 10, 2007.

(51) Int. Cl.
*G01N 30/02* (2006.01)
(52) U.S. Cl. .................................................. 73/61.53
(58) Field of Classification Search .............. 73/61.53
See application file for complete search history.

(56) References Cited

U.S. PATENT DOCUMENTS 6,613,235 B1 * 9/2003 Anderson et al. ............. 210/670
2006/0157647 A1   7/2006 Siuzdak et al.

FOREIGN PATENT DOCUMENTS
WO   WO 2004/017040 A2   2/2004

OTHER PUBLICATIONS

Gu et al., "Capillary array reversed-phase liquid chromatography-based multidimensional separation system coupled with MALDI-TOF-TOF—MS detection for high-throughput proteome analysis," *Journal of Proteome Research* (2006) 5: 3186-3196.

* cited by examiner

*Primary Examiner* — Hezron E Williams
*Assistant Examiner* — Rodney T Frank
(74) *Attorney, Agent, or Firm* — Merchant & Gould P.C.

(57) ABSTRACT

The invention provided is a split-free nano-liter flow liquid chromatography system comprising at least a first and a second chromatographic column connected in series, wherein an autosampler is provided and programmed to inject samples and eluent solutions of increasing eluent concentration for gradually eluting analytes from the first column into the second column (without adversely affecting separation in the second column), said solutions segmented from the mobile phase of the liquid chromatography system by air plugs.

23 Claims, 6 Drawing Sheets

→ Flow　　　SCX　　　　　　C18
　Spray

PLUGGED FLOW 2D CHROMATOGRAPHY

This application claims benefit of Ser. No. 61/012,547, filed Dec. 10, 2007 in the United States and which application(s) are incorporated herein by reference. A claim of priority to all, to the extent appropriate is made.

TECHNICAL FIELD

The present invention provides systems and methods for simultaneously identifying and quantifying individual proteins in complex protein mixtures by multi-dimensional chromatographic and mass spectrographic analysis. The invention also provides computer program products and computer implemented methods for practicing the systems and methods of the invention.

BACKGROUND

Mass spectrometry-based methods for the identification of proteins have become a standard platform in proteomics. The most popular MS-based strategies rely on proteolytic digestion of proteins into peptides before introduction into the mass spectrometer. Digestion of proteins into smaller sized peptides helps to overcome the solubility and handling problems associated with proteins and creates peptide fragments which are easily ionized in the mass spectrometer. Peptide ions are first measured as intact ions, then selected based on their m/z-ratios and subjected to collisionally induced dissociation (CID), in a process known as tandem mass spectrometry (MS/MS). Under the low-energy conditions employed for CID, peptide ions fragment in predictable patterns. Because fragmentation patterns to an extent are predictable, theoretical spectra can be constructed for sequences in protein or nucleotide databases. Computer algorithms can for instance use the CID fragmentation patterns of sample peptides to determine the sequence of the peptide, and this sequence information is used to search against theoretical fragmentation patterns generated from protein and nucleotide databases. Protein identifications are made by finding the best correlation between experimentally derived sequence information and sequences in the database. One of the greatest strengths of tandem mass spectrometry for protein identification is the inherent ability to sequence peptides directly from mixtures. Thus, mass spectrometry allows the direct identification of the individual constituents of protein complexes involved in a wide range of physiological functions. However, if the mixture of peptides is highly complex, it is advantageous to use a separation step prior to analysis to limit the number of peptides the mass spectrometer sees at any given time of the analysis.

One method commonly used to reduce sample complexity prior to introduction into the mass spectrometer is the separation of sample proteins by gel electrophoresis followed by excision of the individual protein spots from the gel and in-gel digestion with a protease (e.g., trypsin). One-dimensional (1D) gels, which separate proteins based on molecular size, provide a low-resolution separation of proteins, but when coupled with tandem mass spectrometry can be used to identify proteins in moderately complex mixtures. For more complex mixtures which are not sufficiently resolved in a 1D separation, a multidimensional separation may be necessary. Multidimensional separations exploit two or more independent physical properties of the proteins or peptides to achieve a higher level of resolution and higher loading capacity than can be achieved in a single dimension. Separation strategies can be selected so that components not separated in the first dimension are separated in the second. Two-dimensional (2D) gels are the most common multidimensional separation technique used to separate proteins in complex mixtures. In this technique, proteins are separated on the basis of their iso-electric point in the first dimension and by their molecular size in the second dimension. The position occupied by a protein on a 2D gel is a reflection of its approximate pI and mass. Although gel-based separations of proteins prior to analysis are effective methods for the analysis of a large number of proteins in complex mixtures, the methods have many shortcomings. One-dimensional gels provide a separation method that is labor intensive, affords limited resolution of proteins, has limited dynamic range, and requires preparation steps that in turn cause decreases in the detection sensitivity by mass spectrometry. To visualize gel-purified proteins so they can be excised and extracted from the gel, the gels must be stained, either by silver staining, Coomassie staining or staining with fluorescent dyes. (Staining gels also allows a quantitative comparison of protein expression, albeit within a limited dynamic range). Two-dimensional gels provide better resolution of proteins but are still labor intensive and have a limited dynamic range. In addition, 2D gels are unable to separate membrane proteins, highly basic proteins or highly acidic proteins under standard conditions.

Gel-based proteomics strategies are rapidly being supplanted by methods that involve peptide separation via high efficiency nano-column liquid chromatography separation techniques directly linked to a mass spectrometer. In these methods, complex protein mixtures are reduced to peptides prior to separation and the total peptide mixture is loaded onto a nanocolumn. The nanocolumn is typically made from fused silica microcapillary tubing that is typically 50-150 µm in inner diameter and has a tip that has been pulled to an inner diameter of 2-15 µm. For single dimensional separations, the nanocolumn is typically packed with reverse-phase C18 material. Once loaded onto the nanocolumn, peptides are eluted into the ionization source of the mass spectrometer, typically using an HPLC acetonitrile gradient. The gradient is run at very low flow rates, typically 100-400 nL/min and the typical elution time per peptide is 10-30 sec. Stable electrospray at the front of the mass spectrometer's inlet orifice is produced when a voltage of 1.8-2.4 kV is applied to the precolumn liquid-metal interface. As peptide ions enter the mass spectrometer, a survey scan of the intact peptides is obtained. Using data-dependent acquisition, the instrument can be set to automatically monitor the survey scan and select peptides based on pre-set criteria such as intensity, charge state or m/z. The selected peptides are fragmented, and MS/MS spectra are collected. By coupling an LC system with a tandem mass spectrometer and data-dependent scanning, it is possible to distinguish individual proteins in complex mixtures containing several hundred components without additional prior purification or separation steps.

While LC-MS/MS is routinely used to sequence peptides and identify proteins directly from complex mixtures, some samples present complexity beyond the separation capacity of a 1D LC technique. To achieve enhanced separation, gel electrophoresis can be employed to separate intact proteins prior to digestion and loading on the nanocolumn. However, this approach is still encumbered by the shortcomings inherent in gel-based techniques. Recently, a higher-resolution and higher-capacity 2D separation has been achieved with an in-line system using a biphasic nano-column. In this technique, known as multidimensional protein identification technology (MudPIT), a 3-5 cm section of strong cation exchange resin (SCX) is placed directly upstream from the C18 resin in the nanocolumn. The SCX segment has a high loading capacity and is upstream from the RP segment, and thus it acts as a peptide reservoir, storing all peptides until a subset of peptide species is "bumped" to the RP segment with incremental increases in salt in the LC gradient. The dislodged peptides are separated on the RP phase column segment using an acetonitrile gradient and, after re-equilibration, another fraction of peptides is displaced from the SCX stationary phase segment to the RP stationary phase segment with an increase in salt concentration. The iterative process of salt bump followed by RP separation is repeated until the reserve of peptides on the SCX is exhausted. This method greatly increases the number of digested proteins that can be analyzed and enhances the detection of low abundance proteins in the mixture.

MudPIT has been used to identify proteins in samples from a wide variety of sources and has been successfully applied to the identification of posttranslational modifications, as well as the quantitative comparison of protein expression using stable isotope labeling. Two-dimensional separation prior to MS/MS has also been performed in discrete steps by performing an SCX separation sequentially followed by multiple RP separations prior to introduction into the mass spectrometer. In this approach, fractions are collected after the sample is run on an SCX column and each fraction is reduced in volume and loaded onto a reverse phase nano-column for LC-MS/MS analysis. One advantage of discrete separation steps over in-line techniques is that it provides more degrees of freedom for sample manipulation and separation optimization between dimensions. Because each separation phase is independent, there is more flexibility in choices for the composition and sizes of the columns and the length of the gradients. However, the independent application of each phase of separation can result in prohibitively long run times and also lead to severe loss of sample in-between steps.

Two-dimensional LC-MS/MS methods have been shown to be useful for many applications, but complex mixtures of peptides frequently contain salts which can interfere with the interaction of the peptides with the SCX resin. For these samples, on-line desalting can be carried out prior to MudPIT using a solid phase extraction column. Alternatively, desalting can be performed online using a triphasic column which contains a 3 cm segment of C18 packing material directly upstream from the SCX segment. In this technique, peptides are desalted in the first cycle and advanced to the SCX segment where they are subject to multidimensional separation. Optimization of MudPIT is dependent on sample concentration, since the sensitivity of peptide detection in the mass spectrometer is determined by the concentration of the peptide eluted from the column. To optimize detection of the lowest abundance peptides, it is typical to heavily load the column, create small increments in the salt "bumps" to displace peptides from the SCX, and run a long RPLC gradient. In this method, it is common to see highly abundant peptides elute over a number of different salt concentrations. Under most circumstances, this will not interfere with the elution and identification of lower abundant peptides. However, with limited sample quantity, longer gradients should be avoided since they may actually decrease detection sensitivity for low abundance peptides. When sample quantity is limited, it is often useful to optimize conditions using a standard protein mixture of similar concentration. With a well optimized separation it is now possible to identify 1500-2000 proteins from a sample derived from a whole cell lysate.

The success of protein mixture analysis by LC-LC/MS-MS depends on the chromatographic step used to introduce the sample into the mass spectrometer. To achieve good chromatography, high quality nano-bore columns are necessary. Only well-packed nano-bore columns will allow the low flow rates (200-300 nL/min) required for femtomole sensitivity. If the column clogs during sample loading, it is frequently a sign that the sample has not been sufficiently purified prior to loading. Occasionally, salts in the sample can interfere with loading and in these situations the clog can be cleared by briefly immersing the column tip in boiling water. It is possible to use nanocolumns more than once, but extreme care must be taken to make sure all previous sample has been stripped from the column prior to re-loading. Columns must be re-equilibrated after stripping and special care must be taken to make sure the solvent flow is satisfactory.

Setting up the experimental parameters and machine instruction necessary to achieve the desired 2D-LC separation can be quite challenging inasmuch as two separate gradients (one for salt buffers and one for organic phase buffers) have to be interleaved and the action of four pumps must be coordinated with great precision. Small inaccuracies can lead to substantial changes in retention times when experiments are being reproduced. In addition to this, the number of control parameters can be quite substantial, making coding errors likely to occur.

Other disadvantages associated with MudPIT analysis is the uncontrolled flow characteristics of conventional split-flow systems, and the corrosive action of the salty buffers used in the ion exchange chromatographic steps. Salt buffers are highly corrosive and often attack the steel and other materials of which the LC pumps and valves are made. This is obviously an increasing problem with prolonged exposure meaning that the pumps and valves used for generating the salt gradient inevitably will fail or be in need of repair. Also high concentration salt buffers tend to cause problems of particulate matter being generated either by precipitation of the salts themselves or by precipitation of the salts formed from corrosive chemical reactions with the LC pump, valve, and tubing materials.

These and other problems have been solved by the present invention.

SUMMARY OF THE INVENTION

The present invention provides a multi-dimensional, especially two-dimensional, three-dimensional, and four-dimensional, chromatography system.

The present inventors have surprisingly found that when a split-free chromatography system and when no mixing of the elution buffers (e.g. salt solutions in an ion exchange column) and the mobile phase of the system takes place, a much more controlled and reproducible system is achieved. Such a system is very suited for automation.

The present invention uses very small volumes of liquid in order to move fractions of analytes from one chromatographic column segment to one or more subsequent chromatographic column segments. This volume is one or several orders of magnitude smaller than the volume that would have to be loaded into and delivered from the actual pumps of quaternary and ternary LC pump systems to achieve the corresponding delivery of solvent in a split-flow LC system. This means that the present invention makes it practically feasible to use labile, corrosive, or toxic eluents and financially feasible to use very expensive eluents such as e.g. a peptide solution. The wider choice of possible eluents also increases the number of usable stationary phases. E.g. the present invention enables the use of stationary phases with one or more immuno-affinity reagents and elution of analytes from said phase by the pertinent hapten(s) dissolved in one or more plugs of liquid that are sequentially drawn from the autosampler. As an example, the stationary phase can contain e.g. TiO2 (titanium dioxide) that binds phosphopeptides and the releasing buffer may contain DHB at relatively high concentration. In both of these examples, a C18-based reverse phase column could provide the chromatographic separation in the second dimension.

The chromatographic separation can be further expanded from being two-dimensional to being multi-dimensional by connecting multiple columns in separate housings or stacking multiple stationary phases in the same housing. With previous practice, each new dimension would require the addition of one or two more pumps and the programming and synchronization of these, and hence on-line multi-dimensional separations have hitherto been nearly unattainable for practical and financial reasons. However, the present invention enables the extension from two-dimensional separation to multi-dimensional separation without increasing the technical complexity or cost of hardware. Each dimension will require its carefully selected eluent, but the only requirement for adding an extra dimension of separation is that the eluent that is active in one dimension does not adversely affect the separation in other dimensions. Normal autosampler systems can easily store a large number of discrete vials, hence this does not pose any practical limit to the number of eluents (and hence dimensions) the overall separation may comprise. As described herein, a single pump can deliver virtually any volume of any liquid from the autosampler and through a column segment of the relevant stationary phase to cause the wanted chromatographic effect, also when a high number of different stationary phases are used. This can be done reproducibly and with precise flow characteristics (flow rate, volume, pressure etc) as long as the pumped flow is delivered by a split-free pumping system and each eluent plug is flanked by air pockets and thereby kept from mixing with the mobile phase that is delivered by the LC pumps. Thus, for example, it becomes straightforward to precede a standard SCX/RP 2-dimensional setup with e.g. poly-affinity columns that selectively bind certain classes of compounds that may be released sequentially by sequential elution with plugs of solvent containing a single competing hapten or released simultaneously by eluting with a single plug of solvent containing a mixture of haptens.

In a preferred embodiment the present invention provides a multi-dimensional, especially two-dimensional, chromatography system comprising an ion exchange column (e.g., a cation or anion exchange column; first dimension) and a reverse phase column (RPC) (second dimension), wherein the ion exchange column and the reverse phase column (RPC) are connected in series. The two columns may be included in a single biphasic nanocolumn; e.g. a 3-5 cm section of strong cation exchange resin (SCX) is placed directly upstream from a C18 resin in the nanocolumn. Alternatively, a piece of transfer tubing may be placed between the two resins and the C18 resin may be split in two separate columns, namely in a trap column and a separating column.

Accordingly, the present invention provides a split-free nano-liter flow liquid chromatography system comprising an ion exchange column and a reverse phase column (RPC) connected in series, wherein an autosampler injects plugs of the salt solutions and segments these from the mobile phase of the liquid chromatography system by air bubbles such that the salt solutions and a the mobile phase will not mix.

In one aspect, the reverse phase column (RPC) is connected to an analytical device on its distal end such that an eluate can be delivered into the analytical device. The analytical device can comprise a mass spectrometer. The mass spectrometer can further comprise a nano-electrospray apparatus. In one aspect, the mass spectrometer comprises a tandem mass spectrometer or an ion trap mass spectrometer or a combination thereof. In one aspect, the ion exchange column (e.g., a cation (CX) or anion exchange column) and the reverse phase column (RPC) are enclosed in one housing. In one aspect, the two dimensions, or columns, are in different housings, or, the columns are arranged such that they can be easily, and individually, replaced.

In one aspect, a flow valve, e.g., a low volume flow valve (e.g., a microvalve) and/or an inline microfilter assembly connects the various columns (e.g., the various housings). For example, in one aspect, each dimension, or column, is in a different housing and one or two of the housings are connected with each other by a flow valve. In one aspect, a flow valve separates the first housing and the second housing.

In one aspect, the system of the invention is fully automated. The system can comprise a sample injector fully integrated with the automated system. In one aspect, the system is integrated to a computer, which can be programmed to run samples on the system, including equilibrating columns, washing, step elution of samples, and the like. In one aspect, an automated system of the invention is used for high throughput proteome profiling with on-line sample collection.

In one aspect, the reverse phase column is packed with a reverse phase resin or a normal phase resin or equivalent. The reverse phase resin can comprise a C 18 reverse phase resin or equivalent. The ion exchange column can comprise a strong cation exchange (SCX) resin or equivalent. The strong cation exchange (SCX) resin can comprise a polysulfoethyl strong cation exchange resin.

In one aspect, the loading capacity is proportional to the column dimension. For example, in one aspect, the loading capacity is approximately 100 μg protein digest per 10 cm×180 μm C18 column, and capacities may include more than milligram sized samples on larger columns.

In one aspect, the chromatography system can further comprise a computer system operatively linked to the chromatography system, thereby making the chromatography an automated operation system. The chromatography systems can further comprise a computer system operatively linked to the mass spectrometer for quantifying the amount of each peptide by use of data from the mass spectrometer.

The chromatography system can further comprise a computer system operatively linked to the mass spectrometer for generating fragment spectra that reveal, at least in part, the sequence of each peptide by use of data from the mass spectrometer.

In one aspect, the liquid chromatography system of the present invention further comprises a computer system operatively linked to the chromatography system, thereby making the chromatography system an automated operation. This computer system enables controlled split-free operation of the liquid chromatography system and ensures that air plugs are introduced between the mobile phase and the salt solutions used to elute analytes from the ion exchange column.

In one aspect, the liquid chromatography system further comprises a computer system operatively linked to a mass spectrometer for quantifying the amount of each peptide by use of data from the mass spectrometer. In one aspect, the liquid chromatography system further comprises a computer system operatively linked to the mass spectrometer for generating the sequence of each peptide by use of data from the mass spectrometer.

The present invention further provides a method for separating polypeptides comprising the following steps:

(a) injecting a sample comprising polypeptides onto an ion exchange column; and (b) separating the peptides by chromatography to generate an eluate using the chromatography system of the present invention, wherein polypeptides are eluted from the ion exchange column by injecting salt solutions with increasing salt concentration, said salt solutions being flanked by air plugs in order to avoid contact of salt solutions with the mobile phase of the chromatography system.

The invention also provides a computer-implemented method for analyzing data generated by the chromatography system of the present invention comprising the following steps: (a) providing a chromatography system capable of outputting data to a computer; (b) providing a computer capable of storing and analyzing data input from the chromatography system comprising a computer program product embodied therein, wherein the computer program product comprises a computer program product of the invention; (c) inputting the data from the chromatography system into the computer and analyzing data input from the chromatography system.

Entering analysis instructions and parameters for 2-dimensional chromatography can be a complicated and tedious process on systems that employ four intermittently active chromatographic pumps for providing the two consecutive gradients (i.e. a piece of salt buffer gradient followed by a full organic phase gradient in repeated steps). The present invention permits a simplification of the man-machine interface to be made, namely by using a software interface that expands the systems normal 1-dimensional method instruction set by only two parameters in order to become a fully working 2-dimensional separation method. These two parameters would in that case be a simple "check box" to turn on the 2-dimensional mode, and the number of salt plugs to be injected (from pre-defined positions on the sample plate then). In other words, the present invention provides a means for performing 2-dimensional separation not only with simpler instrumentation than commonly used for the purpose but also much simpler method definitions. These two simplifications in combination turn 2-dimensional separation into a process as easy and robust as the process used for 1-dimensional separation.

Thus, in one aspect the chromatography system utilizes a user interface requiring only two additional experimental parameters to be entered in order to switch from one-dimensional chromatography to two-dimensional chromatography. In this respect there is also provided a chromatography system of the present invention, wherein the autosampler positions for salt buffers have been predefined and stored in system settings such that these positions need not be entered by users for each analysis. These autosampler positions for salt buffers can be stored as multiple sets of positions, each of which can be named and retrieved from a data structure by users when subjecting samples for analysis.

In relation to the switching from 1D to 2D the chromatography system is provided with a software checkbox or similar interface, which signifies that an analysis is meant to be two-dimensional rather than one-dimensional and the only other experimental parameter required be the number of salt steps that make up the first dimension separation.

DETAILED DESCRIPTION

Figure 1:
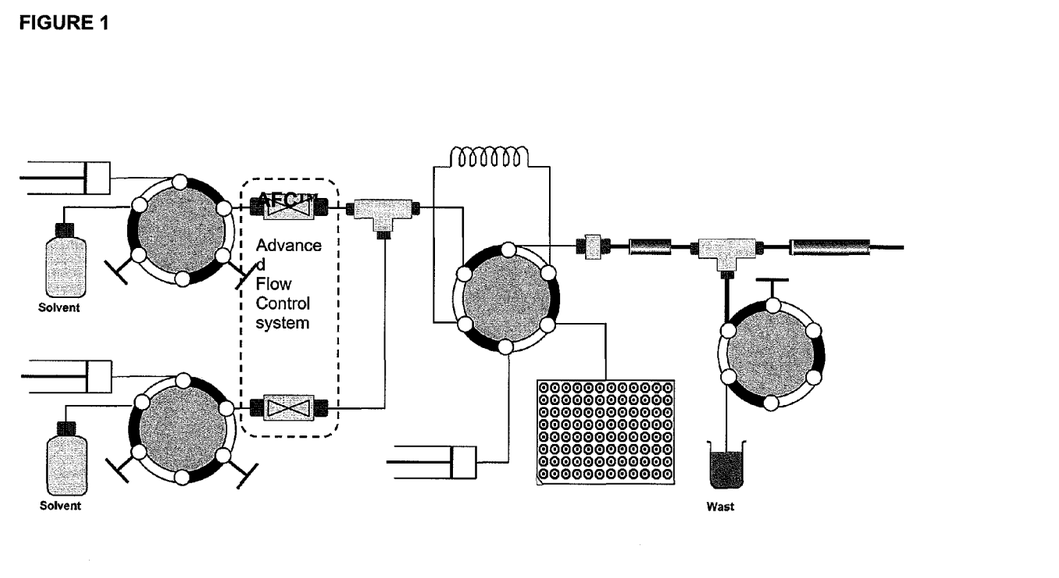
FIG. 1 is a schematic drawing of the collective flow path of the 1-dimensional chromatography system of the present invention.
Figure 2A:
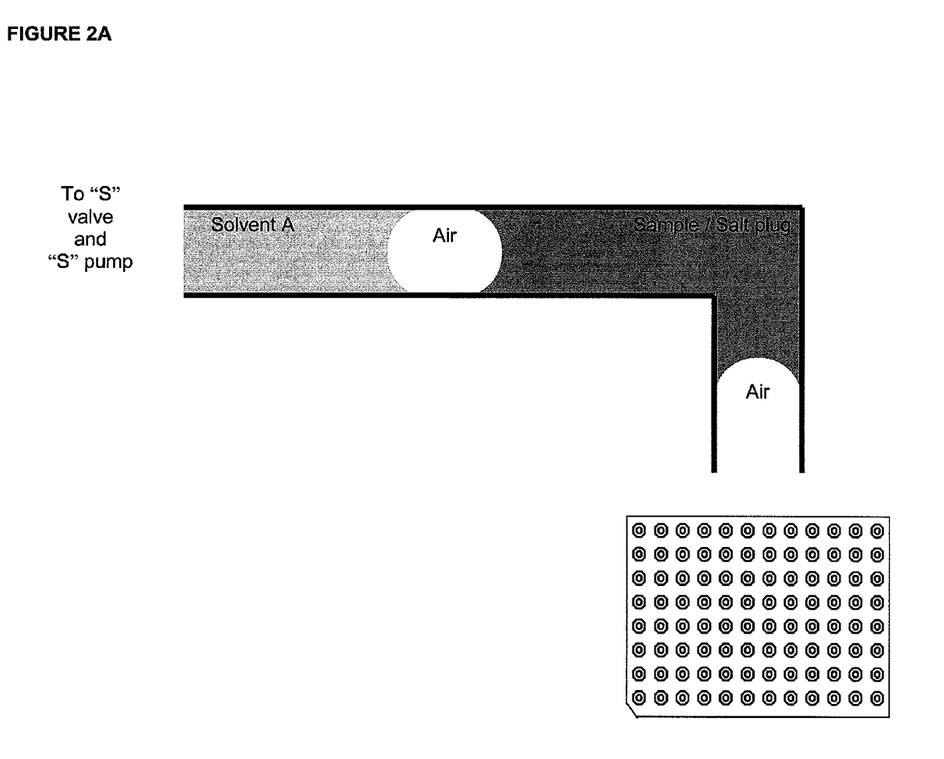
FIG. 2A is a schematic drawing of the autosampler flow line while a sample or salt plug is being picked up from a sample or salt buffer vial, respectively. As can be seen, the sample or salt plug is kept separate from the mobile phase of the chromatography system by a small air bubble that typically has a volume of one µL.
Figure 2B:
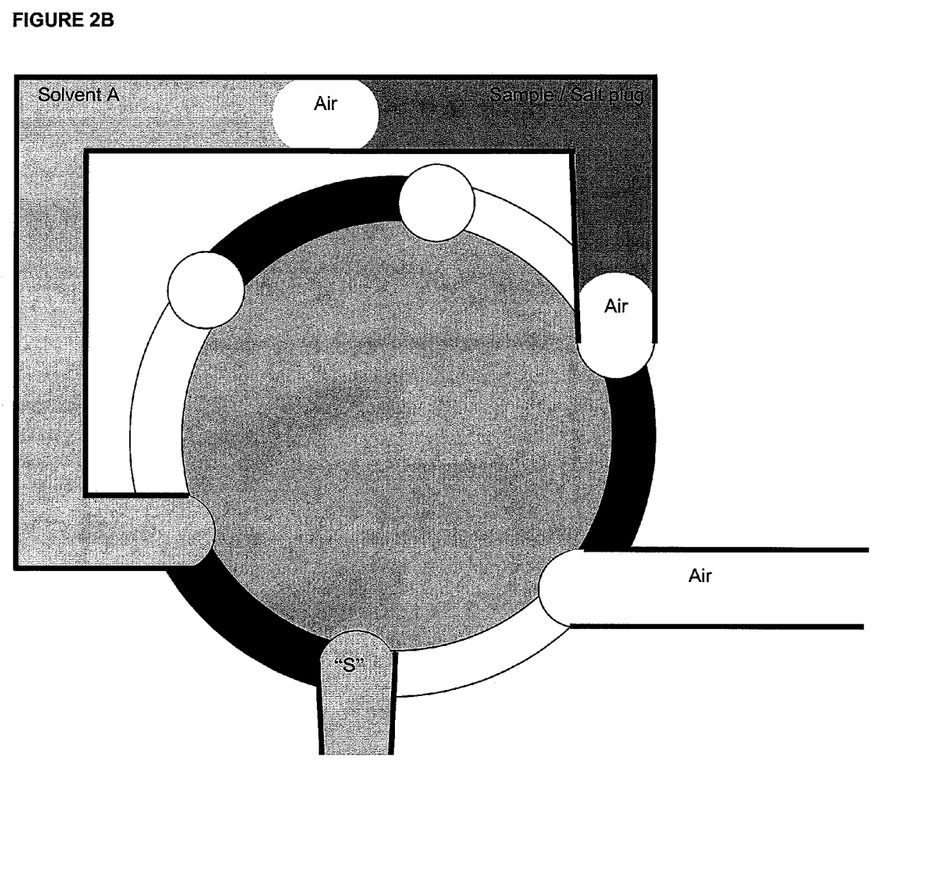
FIG. 2B is a schematic drawing of the sample or salt plug at the position of the sample loop of the chromatography system with the air bubbles bracketing the solution.
Figure 2C:
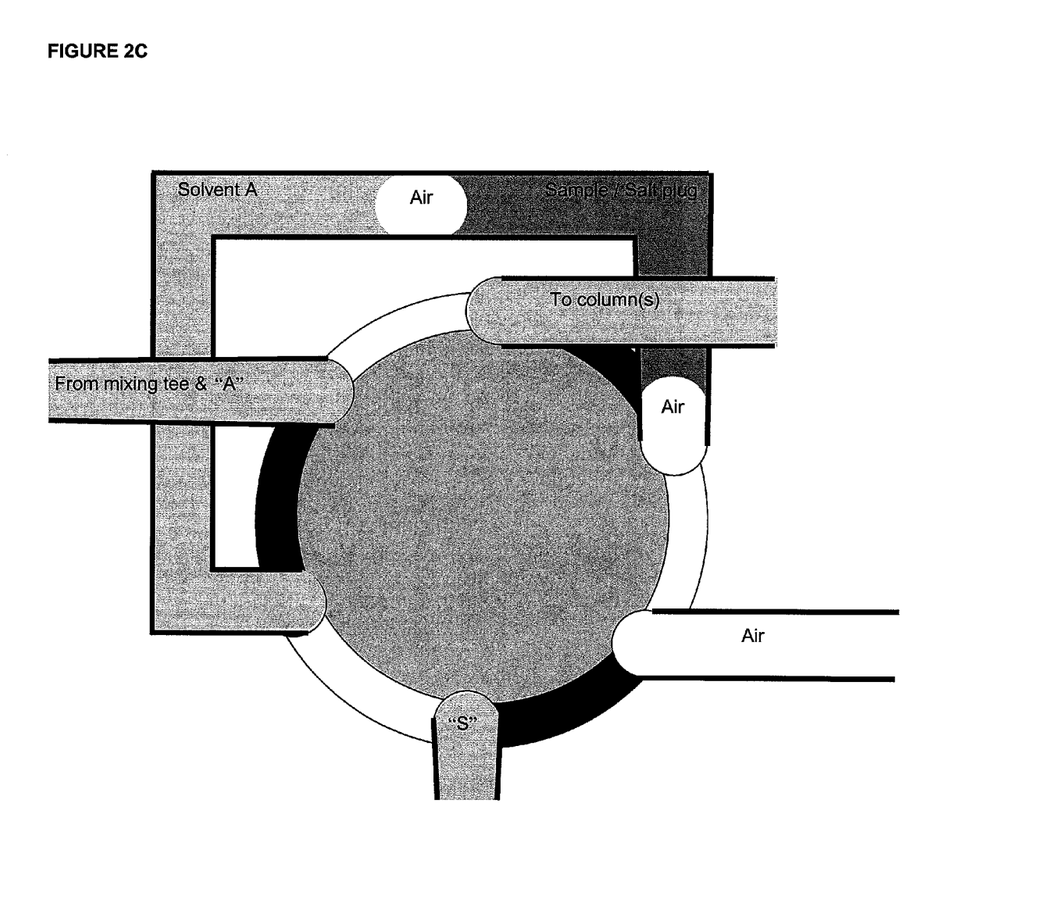
FIG. 2C is a schematic drawing of the sample loop after the valve has been switched such that the A-buffer pump may cause the sample or salt plug (with bracketing air bubbles) onto the bi-phasic stationary phase of a chromatography column (e.g. SCX material followed by C18 material).
Figure 3:
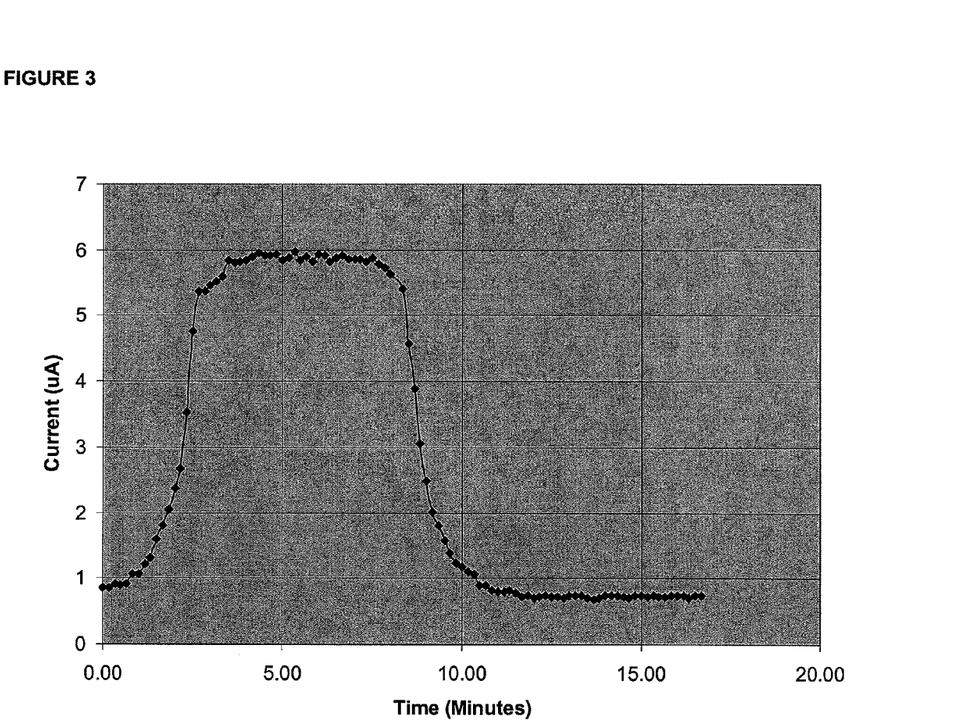
FIG. 3 is a graph of the spray current of an electrospray mass spectrometer source as a function of time, recording during the injection of a 4 µL 125 mM ammonium-acetate plug at a flow rate of 600 nL/min. As should be expected with this flow rate and volume, the salt plug causes a rise in spray current for nearly 7 minutes. As can be seen from the fast rise times and fall times, as well from the relatively flat steady state spray current, the salt plug remains of uniform concentration throughout its volume (both longitudinal and radial dimensions).
Figure 4:
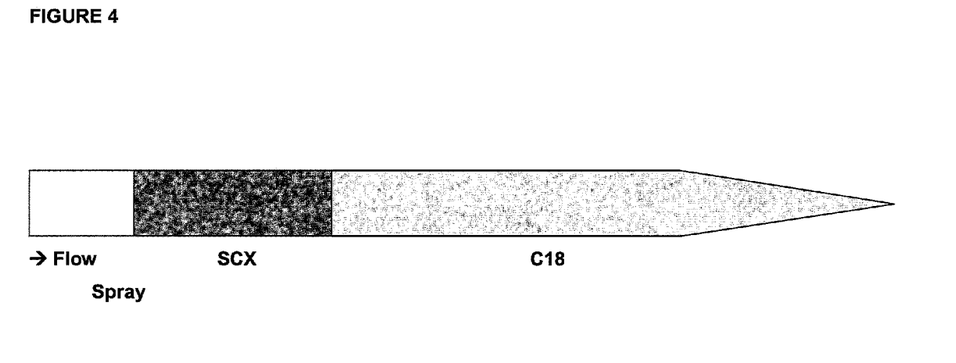
FIG. 4 is a schematic drawing of a bi-phasic chromatography column made such that the stationary phase is packed directly inside a piece of fused silica tubing that also serves as the electrospray emitter.

The present invention improves the resolution of molecules in a sample by providing multidimensional liquid chromatographic fractionation of the sample, prior to further separation of the molecular constituents of the sample by spectrometry. The LC$^n$ apparatus of the present invention takes advantage of a first and second column to fractionate molecules based on different physical properties. For example, the first and second column may separate molecules on the basis of hydrophobicity (e.g., with a RP column) and net charge (e.g., with a SCX column), respectively. The first two columns may be configured in tandem, with the first and second resins directly adjoining one another, to provide a rapid, in-line means of initial fractionation of molecules in a sample, even though a tandem arrangement does not allow a truly orthogonal separation of molecules in the sample.

The present invention may substantially improve molecular resolution by providing at least one additional LC column that further resolves molecules eluted from the first two columns. Molecules eluted from the at least one additional column may be inserted into a mass spectrometer for final resolution of the molecular components. As a result of the at least third dimension of liquid chromatography added by the present invention, the overall complexity of the sample fraction that is analyzed in any single mass spectrometer run is reduced, allowing more components to be resolved from each other and increasing the dynamic range of resolution. Peak capacity may be increased as well, particularly in an embodiment where the additional column(s) comprise a high-resolution, analytical column.

Various combinations of suitable liquid chromatography resins and geometries for the LC columns of the LC$^n$ apparatus are possible. A "separation characteristic" can relate to physical basis by which the resin resolves and separates molecules, such as by net charge, size or hydrophobicity. A combination of resins in the present invention thus could include three resins that separate molecules by different physical characteristics, such as a combination of size exclusion, ion exchange and reversed-phase resins. A difference in "separation characteristics" also can refer to a difference in the number of theoretical plates of the column. Thus, the present combination of resins could include two types of resins rather than three, where a third column has a geometry providing a higher number of theoretical plates, giving the third column greater resolution and separation characteristics than either the first or second columns.

An in-line trapping column at the terminus of the second LC column may be used in one embodiment of the present invention to facilitate the use of different flow rates and solvents for elution of additional columns within the $LC^n$ apparatus. The trapping column alternately communicates with the outlet of the second LC column and the head of a third column. That is, the trapping column first may be positioned in tandem with the second column to trap molecules that are eluted from the second column. The trapping column then may be repositioned to the head of the third column so that the trapped molecules may be eluted from the trapping column onto the third column.

Use of the trapping column allows the third column to be eluted under conditions that otherwise might be incompatible with optimal separation by the first two columns. For instance, if the third column were positioned in tandem with an ion exchange second column, eluting the third column with a solute gradient also might cause some of the molecular species bound to the upstream ion exchange column to be eluted. Instead, the sample fraction bound to the trapping column may be eluted onto the third column without disturbing the fractionation of molecules provided by the first two columns.

Repositioning of the trapping column from the second to the third column may be accomplished by a switch-valve. The switch-valve may be may be fully automated to facilitate high-throughput use of the apparatus. High-pressure reversible fittings known in the art may connect the trapping column connection with the LC columns. These fittings may be designed and utilized by means well known in the art to minimize disruption in the fluid flow between the various columns to minimize peak broadening.

Multi-dimensional liquid chromatography has been previously reported in various incarnations involving reverse phase columns coupled to either cation exchange columns or size exclusion columns. However, it was only when the technique was employed with a mixed bed microcapillary column containing strong cation exchange (SCX) and reverse phase chromatography (RPC) resins that the true utility of this separation technique was demonstrated. The present invention involves further improvements to this technique.

The method of operating the chromatography system of the present invention involves a number of steps. Below there is provided a description of how the system is operated when analysing a protein sample.

First, a denatured and reduced protein mixture is digested with trypsin to produce peptide fragments. The mixture is loaded onto a microcapillary column containing SCX resin upstream of RPC resin and eluting directly into a tandem mass spectrometer via electrospray ionization. A discrete fraction of the adsorbed peptides are displaced from the SCX column onto the RPC column using a step gradient of salt, causing the peptides to be retained on the RPC column while contaminating salts and buffers are washed through. Peptides are then eluted from the RPC column using e.g. an acetonitrile gradient, and analyzed by MS/MS.

This process is repeated using increasing salt concentration to displace additional fractions from the SCX column. This is applied in an iterative manner, typically involving 6-24 steps, and the MS/MS data from all of the fractions are analyzed by database searching and combined to give an overall picture of the protein components present in the initial sample. This technique can be run in a fully automated system. The use of two dimensions for chromatographic separation greatly increases the number of peptides that can be identified from very complex mixtures. In one typical run up to 3000 proteins can be identified with high confidence. In order to identify more proteins from complex protein samples, one has to reduce protein complexity.

In one exemplary protocol, first, a denatured and reduced protein mixture is digested with trypsin to produce peptide fragments. Without desalting, the mixture is directly loaded onto a microcapillary column containing SCX resin and RPC resin, and eluted directly into a tandem mass spectrometer. This process is carried out by using increasing salt concentration to displace additional sub-fractions from the SCX column following each step by a reverse phase gradient. Each cycle is applied in an iterative manner, and depends on the complexity of the peptides. Normally it involves 5-15 salt steps.

Both quantity and sequence identity of the protein from which the modified peptide originated is determined by multistage MS. This is achieved by the operation of the mass spectrometer in a dual mode in which it alternates in successive scans between measuring the relative quantities of peptides eluting from the capillary column and recording the sequence information of selected peptides. Peptide sequence information is automatically generated by selecting peptide ions of a particular mass-to-charge (m/z) ratio for collision-induced dissociation (CID) in the mass spectrometer operating in the tandem MS mode.

The resulting tandem mass spectra are correlated to sequence databases to identify the protein from which the sequenced peptide originated. Commercial available software that may be used is Turbo SeQuest by Thermo Finnigan, Mascot by Matrix Science, and Sonar MS/MS by Proteometrics. Special software has been developed for automated relative quantification, including MS Quant from the Max Planck Institute in Martinsried, Germany.

The present application provides a non-gel based method of identifying individual proteins in complex protein mixtures simultaneously and quantifying protein expression level globally. It overcomes the limitations inherent in traditional techniques.

EXAMPLE

In the present example a 1-2 cm section of strong cation exchange resin (SCX) is placed directly upstream from an approximately 10 cm long section of C18 resin in the nano-column. The SCX segment acts as a peptide reservoir, storing peptides until a subset is "bumped" to the RP segment with incremental increases in salt in the LC gradient. The dislodged peptides are separated on the RP phase using an acetonitrile gradient and, after re-equilibration, another fraction of peptides is displaced from the SCX to the RP with an increase in salt concentration. The iterative process of salt bump followed by RP separation is repeated until the reserve of peptides on the SCX is exhausted. This method greatly increases the number of digested proteins that can be analyzed and enhances the detection of low abundance proteins in the mixture.

A nano-flow HPLC without a flow splitter is used in accordance with the present invention. The nano-litre pumps of the HPLC use a direct drive sapphire piston and are completely pulsation-free which eliminates the repetitive, physical shocking of all liquid parts and separation columns, giving fewer leaks and less downtime. The direct drive pumps allow very precise, split free binary gradient mixing, controlled by two nano flow sensors, one for each mobile phase.

In an exemplary experiment, the aim was to identify the cytosolic proteins in mouse placental cells. To this end, the cytosolic fraction was subjected to cysteine reduction and alkylation with iodoacetamide then digested with trypsin. The digest solution was pre-cleaned by C18-based solid phase extraction and an aliquot loaded into a sample vial that was placed in the autosampler of an EasyLC (Proxeon Biosystems, Denmark) along with 9 other vials containing increasing concentrations of ammonium acetate dissolved in buffer A (i.e. the A-phase of the two mobile phases used in generating the organic gradient for elution of peptides from the C18 section). Table 1 lists the autosampler load and salt concentrations used.

The bi-phasic column that was used, contained an SCX trapping section (~2 cm×ID 75 μm) and the C18 capillary analytical column (~8 cm×ID 75 μm), made in one integrated unit along with the electrospray emitter. This was made by packing an appropriate pulled fused silica emitter with the two slurries in sequence (i.e. first C18, then SCX), The key parameters of the actual separation step were as follows:
a) for the sample loading step:
Initial 3 μl column equilibration at 600 nL/min.
10 μl sample pickup,
25 μl sample injection at 600 nL/min.
2 h gradient
Salt "bump" runs:
3 μl column equilibration at 600 nL/min.
4 μl "salt sample" pickup,
10 μl sample injection at 600 nL/min, and
2 h gradient An OrbiTrap mass spectrometer (ThermoFinnigan, Bremen, Germany) was used for this study. Peptides eluted from the microcapillary column were directly electrosprayed into the mass spectrometer with the application of a ~1.7 kV spray voltage.

TABLE 1

| Well # | % 0.5M NH4Ac in Buffer A |
|---|---|
| 1 | Sample |
| 2 | 10 |
| 3 | 20 |
| 4 | 25 |
| 5 | 30 |
| 6 | 35 |
| 7 | 40 |
| 8 | 60 |
| 9 | 80 |
| 10 | 100 |

Table 1 is a list of contents of ten vials on the autosampler from which first the sample and afterwards nine increasingly concentrated salt plugs were drawn in the experiment described herein.

TABLE 2

| Scoring Criteria | 1D | 2D-1 | 2D-2 | Combined 2D |
|---|---|---|---|---|
| Peptide Prophet 95% 2 unique peptide minimum | 413 | 1220 (×2.95) | 1390 (×3.37) | 1604 (×3.88) |
| Peptide Prophet 95% 1 peptide minimum | 524 | 1461 (×2.79) | 1670 (×3.19) | 1906 (×3.64) |
| X! Tandem e score <−2.0 2 unique peptide minimum | 476 | 1338 (×2.81) | 1540 (×3.26) | 1788 (×3.76) |
| X! Tandem e score <−1.5 2 unique peptide minimum | 518 | 1439 (×2.78) | 1656 (×3.20) | 1907 (×3.68) |
| X! Tandem e score <−2.0 1 peptide minimum | 788 | 2171 (×2.76) | 2354 (×2.99) | 2673 (×3.39) |

Table 2 shows the number of proteins that were identified as a function of (in horizontal rows) different search parameters and two different software applications for identifying proteins based on MS/MS data; and as a function of (in vertical columns) the chosen method of peptide separation prior to MS/MS analysis in a mass spectrometer. Using the 1-dimensional separation as the yardstick, the numbers in parenthesis represent the factor of increase in the number of identified protein obtained by using 2-dimensional separation. 2-dimensional separation was performed in duplicate to show the consistency in the number of identifiable proteins.

The table shows that, independently of the stringency of the database search (conversion of MS/MS data to protein identification), 2-dimensional separation yields 3 times more identifications than 1-dimensional. The comprehensiveness of the catalog of proteins in a sample is a key success criterion and analyses based on 2-dimensional separation are clearly much more successful. Also shown in table 2 is a column with the number of proteins identified by pooling the MS/MS data from the two repeat 2-dimensional analyses. This process yields around 4 times more identified proteins than a 1-dimensional analysis, while it is still performed automatically and with very simple equipment.

The invention claimed is:

1. A split-free nano-liter flow liquid chromatography system comprising at least a first and a second chromatographic column connected in series, wherein an autosampler is provided and programmed to inject samples and eluent solutions of increasing eluent concentration for gradually eluting analytes from the first column into the second column, without adversely affecting separation in the second column, said solutions segmented from the mobile phase of the liquid chromatography system by air plugs, wherein the first column is an ion exchange column and the second column is a reverse phase column, said eluent solutions being in the form of salt solutions, and said reverse phase column (RPC) is optionally connected to an analytical device such that an eluate can be fed into the analytical device.

2. The method of claim 1, wherein the analytical device comprises a mass spectrometer.

3. The chromatography system of claim 2, wherein the mass spectrometer further comprises a nano-spray apparatus.

4. The chromatography system of claim 2, wherein the mass spectrometer comprises a tandem mass spectrometer or an ion trap mass spectrometer or a combination thereof.

5. The chromatography system of claim 1, wherein the ion exchange column and the reverse phase column (RPC) are enclosed in one housing.

6. The chromatography system of claim 1, wherein the reverse phase column is packed with a reverse phase resin or equivalent.

7. The chromatography system of claim 6, wherein the reverse phase resin comprise a C 18 reverse phase resin or equivalent.

8. The chromatography system of claim 1, wherein the ion exchange column comprises a cation exchange (CX) column or an anion exchange column.

9. The chromatography system of claim 8, wherein the cation exchange (CX) column comprises a strong cation exchange (SCX) resin or equivalent.

10. The chromatography system of claim 9, wherein the strong cation exchange (SCX) resin comprises a polysulfoethyl A strong cation exchange resin.

11. The chromatography system of claim 1, further comprising a computer system operatively linked to the chromatography system, thereby making the chromatography system an automated operation.

12. The chromatography system of claim 2, further comprising a computer system operatively linked to the mass spectrometer for quantifying the amount of each peptide by use of data from the mass spectrometer.

13. The chromatography system of claim 2, further comprising a computer system operatively linked to the mass spectrometer for generating the sequence of each peptide by use of data from the mass spectrometer.

14. The chromatography system of claim 1, further comprising on-line sample collection apparatus.

15. The chromatography system of claim 1, wherein the operation is fully automated.

16. A method for separating peptides comprising the following steps:
    (a) providing a sample comprising peptides; and
    (b) separating the peptides by chromatography to generate an eluate using a chromatography system as set forth in claim 1, wherein eluent solutions of increasing eluent concentration are injected in the first column for gradually eluting analytes from the first column into the second column, wherein the eluent solutions are flanked by air plugs.

17. The method of claim 16, wherein the first column is an ion exchange column and the second column is a reverse phase column, said eluent solutions being in the form of salt solutions.

18. The method of claim 16, wherein the peptides are generated by enzymatic digestion or by nonenzymatic fragmentation.

19. The method of claim 16, wherein a salt gradient and a reverse phase gradient elution is
    performed by the chromatography system, said reverse phase gradient comprises ($X_n$–$X_n$+% B) over 120 minutes with a flow rate of 250 nl/min, and B comprises a buffer B comprising 80% ACN/0.1% formic acid, or equivalent, and n is an integer, n=O, 1, 2, 3, etc.

20. The method of claim 19, wherein the salt gradient comprises a series of salt elusion steps.

21. The method of claim 20, wherein upon the completion of a series of salt elusion steps, the entire elusion sequence is repeated, employing a higher reverse phase gradient.

22. The method of claim 21, wherein the salt gradient steps comprise 12 salt gradient steps comprising 25 mM, 50 mM, 75 mM, 100 mM, 125 mM, 150 mM, 175 mM, 200 mM, 225 mM, 250 mM, and 2 M ammonium acetate, or equivalent.

23. The method of claim 22, further comprising use of a computer-implemented method for analyzing data generated by a chromatography system comprising the following steps:
    (a) providing a chromatography system capable of outputting data to a computer;
    (b) providing a computer capable of storing and analyzing data input from the chromatography system comprising a computer program product embodied therein; and
    (c) inputting the data from the chromatography system into the computer and analyzing data input from the chromatography system.

* * * * *